United States Patent [19]

Ogle, II

[11] Patent Number: 4,813,406
[45] Date of Patent: Mar. 21, 1989

[54] ORTHOPEDIC SPLINT ARRANGEMENT

[75] Inventor: George B. Ogle, II, Alta Loma, Calif.

[73] Assignee: IMS Limited, South El Monte, Calif.

[21] Appl. No.: 877,897

[22] Filed: Aug. 6, 1986

Related U.S. Application Data

[60] Division of Ser. No. 734,328, May 15, 1985, Pat. No. 4,644,941, which is a continuation-in-part of Ser. No. 612,683, May 21, 1984, abandoned.

[51] Int. Cl.$^4$ .............................................. A61F 5/04
[52] U.S. Cl. ............................... 128/87 A; 128/87 R; 128/77
[58] Field of Search ............... 128/87 A, 87 R, 160, 128/132, 157, 77

[56] References Cited

U.S. PATENT DOCUMENTS

| | | | |
|---|---|---|---|
| 1,684,076 | 9/1928 | Smith | 128/87 A |
| 1,817,212 | 8/1931 | Siebrandt | 128/87 A |
| 1,837,691 | 12/1931 | Thigpen | 128/87 A |
| 2,273,028 | 2/1942 | Eaton | 128/87 A |
| 2,528,456 | 10/1950 | Stevenson | 128/87 A |
| 3,794,019 | 2/1974 | Ritland et al. | 128/87 A |
| 3,938,510 | 2/1976 | Gerber | 128/87 A |
| 4,103,682 | 8/1978 | Franzl | 128/87 A |
| 4,441,489 | 8/1984 | Evans et al. | 128/87 A |
| 4,644,941 | 2/1987 | Ogle, II | 128/87 A |

FOREIGN PATENT DOCUMENTS

| | | | |
|---|---|---|---|
| 2290921 | 6/1976 | France | 128/87 A |
| 2417973 | 10/1979 | France | 128/87 A |

*Primary Examiner*—C. Fred Rosenbaum
*Assistant Examiner*—Mark F. Colosimo
*Attorney, Agent, or Firm*—Christie, Parker & Hale

[57] ABSTRACT

A splint device for the immobilization of a preselected portion of the body, such as a digital member. The splint device preferably comprises a splint means comprising a ring-like base portion adapted to fit snugly around a digit in proximity to its proximal end. Extending from the base portion there are provided a plurality of essentially rigid elongated support members which are spaced apart around the base portion so as to immobilize the contained digit, preferably on more than one of its sides, each of the support members terminating at a free end which is in the vicinity of, or beyond the distal end, of the digit. The ring-like base portion is preferably expandable. The splint device may also comprise restraining means which may be positioned around the support member for retaining the support members adjacent the digital member, and an end cap which may be positioned on the free ends of the support members.

44 Claims, 7 Drawing Sheets

ORTHOPEDIC SPLINT ARRANGEMENT

This application is a division of application Ser. No. 734,328, filed May 15, 1985 now U.S. Pat. No. 4,644,941 which was a continuation in part of Ser. No. 612,683 filed 5/21/84 now abandoned.

BACKGROUND OF THE INVENTION

1. Field of the Invention

This invention relates to the medical arts, and, more particularly, to an improved splint arrangement for immobilizing preselected portions of the body.

2. Description of the Prior Art

In many applications it is desirable to provide for immobilization of a body member. For example, a bone fracture may require immobilization during the time period when the bone is healing. Bruises or other injuries to various members of the body may also require immobilization of such body member to prevent exacerbation of the injury or bruises to the body member.

Preferably, the splint devices to be used for these purposes are light in weight and of minimal size, to avoid undesired encumbrance, but still provide the desired type of protection and/or immobilization. Additionally, the splint devices should be inexpensive to fabricate and use. During utilization the splint device is preferably comparatively quickly and easily installable on and removable from the body member by the appropriate attending personnel. Such a feature facilitates not only the initial installation of the splint device, but also removal thereof with minimal discomfort, so as to allow inspection and/or treatment of the body member. Care must be taken, however, in many applications, to insure that the device is "childproof," that is, not easily removable or manipulatable by children.

Paramedics and other emergency attending personnel, in particular, require splint devices which may be rapidly installed on the fractured or otherwise injured body member.

Another desired feature is that one splint device be adaptable to a variety of sizes of body members so that the inventory of the attending personnel may be minimized. A semi-rigid construction is also desired in many applications of a splint device to allow conformation of the splint device to a particular shape of the body member. Of course, the splint device must have sufficient strength and rigidity to provide the protection desired on any specific application.

The prior art devices utilized as splints or otherwise, to immobilize or otherwise protect a fractured or injured body member have not always met the above desiderata.

In some prior art applications, various types of rigid splints have heretofore been used to immobilize broken bones in body members, including arms, legs, fingers, and toes. Rigid plaster casts are also utilized for this purpose.

U.S. Pat. No. 1,144,103 discloses a finger splint consisting of a pair of thin pliable strips, secured together at their centers, to extend at right angles to each other, the strips being bent inwardly toward each other at a point adjacent the center to form an elongated framework, the free ends of said strips being provided with slots.

U.S. Pat. No. 1,229,633 describes a finger guard consisting of a plurality of strips of pliable metal, wire, or other suitable material, twisted about each other upon their approximate centers in such a manner that a plurality of extensions result, which, upon being bent or contoured to the finger, extend in a substantially parallel relation. The guard is adapted to be held in place on the member by adjesive strips, cord, or other suitable means.

U.S. Pat. No. 3,692,022 describes a digital splint adapted for use on a finger. The splint includes a generally cylindrical, rigid, hollow member, in which the finger is inserted, and a spring clip member which engages the finger through a pair of mutually opposed slots in the hollow member, and which secures the hollow member to the finger.

In U.S. Pat. No. 2,573,715, there is described a splint consisting of a pair of substantially parallel legs having transverse weakened parts therein for ready removal of a portion of each leg. The weakened parts define removable portions of the legs. The legs are connected at one pair of ends thereof by means of an integral part of the splint.

U.S. Pat. No. 2,506,464 pertains to what is referred to as a finger stall, comprising a plurality of strips of malleable material, the strips being pivotally held together one upon the other at their central portions, the strips being pivotally turnable out of registry with each other and the ends of the strips being turned in the same direction form U-shaped elements having parallel positioned legs which are pivotally adjustably positionable around an injured member, one leg element is curved transversely to provide stiffness to the leg and to provide a formed curvature in the stall for close fitting around the injured member.

Another splint is disclosed in U.S. Pat. No. 2,022,883. This splint has a paddle shaped semi-pliable plate of a material having the inherent quality of being easily bent manually into various forms, and of retaining such forms when so bent. The plate has a substantially rectangular blade portion, and a portion of the blade continuing from one end thereof and gradually decreasing in width at one side of its axis and somewhat more abruptly decreasing in width at the other side of its axis. Digits can be bandaged to the blade.

Finally, U.S. Pat. No. 1,245,858 relates to a surgical splint consisting of a pair of pliable strips adjustably connected together between their ends and extending at substantially right angles to each other. The strips are bent in parallel relationship for engagement upon a finger.

In contrast to the foregoing, the present splint device meets the above mentioned desiderata, and is unique in providing a simple device for effective immobilization and protection of a broken or injured body member. A splint device according to the principles of the present invention is adaptable to a wide range of body member sizes and is adjustable thereto and securely retainable thereon. The device does not retain water or perspiration.

The splint device of the present invention is inexpensive, comparatively light in weight, of minimal bulk, and may be rapidly and easily installed on the body member. "Childproofing" of the splint device may also be provided.

It will be appreciated that while the splint device described herein is shown as utilized on human body members, the invention is not so limited. Splint devices of the present invention may also be utilized advantageously in veterinary medicine in treatment of animals.

Further, while the invention is described herein as utilized on body members comprising digits, such as fingers or toes, it will be appreciated that the present invention is not so limited. Splint devices in accordance with the principles of the present invention may be utilized on other body members whose shape and conformation are adaptable for such use.

SUMMARY OF THE INVENTION

Accordingly, it is an object of the present invention to provide an improved splint device for immobilization and/or protection of a body member.

It is another object of the present invention to provide an improved lightweight and inexpensive splint device.

It is another object of the present invention to provide a splint device that is rapidly and easily installable and removable and yet may be made "child-proof."

It is yet another object of the present invention to provide a splint device that is adjustable to fit a variety of body members and also allow rapid adjustment to accommodate swelling of the body member.

In a preferred embodiment, the present invention comprises a splint device for the immobilization of a body member because of fractures or other injuries to the body member. Such a body member may, for example, be a digit, such as a finger or toe. The splint device comprises a splint means comprising a ring-like base portion adapted to fit around a digit in proximity to the digit's proximal end. Extending from the base portion, there is provided a plurality of essentially rigid or semi-rigid elongated support members which are coupled to the base portion of their base ends and are spaced apart around the base portion. The elongated support members are positionable adjacent the contained digit, preferably on more than one of its sides. Each of the support members terminates at a free end which is in the vicinity of, or beyond, the distal end of the digit. Support members may be "mushroom" type projections and the retaining means may be a comparatively flexible strap. The flexible strap has walls defining a mushroom engaging slot and is provided with a plurality of self retaining clasp means thereon to allow adjustment to any desired diameter as it is wrapped around the support members.

Another feature disclosed in U.S. patent application Ser. No. 612,683 is cap means which may be installed over the free ends of the support members for retention thereon. The cap means may, if desired, be made "child-proof" to prevent the undesired removal of the cap means by small children.

Yet another embodiment disclosed in U.S. patent application Ser. No. 612,683 is that the ring-like base portions may be of a fixed diameter or, alternatively, may be provided with radial expansion capability to provide a predetermined circumferential expansion. The radial expansion capability may be achieved by axially extending slots, by "zig-zag" interconnections between the support members, or combinations thereof. The circumferential expansion characteristic permits utilization of one sized splint device on a variety of sizes of body members.

The above described embodiment of the invention disclosed in U.S. patent application Ser. No. 612,683, which incorporates a radial expansion capability, if the ring-like base portion permits utilization thereof, on a variety of body members other than digits. However, the limitations imposed by the maximum radial expansion capability of the ring-like base portion tends to limit the body members upon which interconnections between the support members, or combinations thereof.

The circumferential expansion characteristic permits utilization of one sized splint device on a variety of sized body members.

It will be appreciated, of course, that the various features of each embodiment of the present invention may be combined, as appropriate, for any given application of the improved splint device of the present invention.

BRIEF DESCRIPTION OF THE DRAWING

The above and other embodiments of the present invention may be more fully understood from the following detailed description, taken together with the accompanying drawing, wherein similar reference characters refer to similar elements throughout, and in which.

DESCRIPTION OF THE PREFERRED EMBODIMENT

Referring now to the drawing, and particularly FIGS. 1 to 7, there is illustrated an embodiment, generally designated 2, of the present invention. In the embodiment 2, there is provided an improved splint device generally designated 4.

The splint device 4 is comprised of a splint means 6 having a base portion 10. The base portion 10, in the embodiment 2, has a fixed circumferential dimension. That is, the base portion 10 does not have expansion capability. The base portion 10 is fabricated to be in a ring-like configuration as illustrated. However, in the preferred embodiment of the present invention the splint device 4 is semi-rigid, that is, it has a predetermined degree of flexibility to allow utilization as described herein, but still has sufficient rigidity to provide the immobilization of the body part to which it is applied.

It will be appreciated that while the embodiments of the splint devices shown herein are illustracted as utilized on body portions comprising digits, for example, fingers (FIG. 1) and toes (FIG. 2), the present invention is not so limited and may be advantageously utilized on other appropriate body portions.

The splint device 4 also comprises a plurality of elongated support members 12 having base ends 11 coupled to the base portion 10 and free ends 13. In the embodiment 2, the support members 12 are unitarily fabricated with the base portions 10 by, for example, molding so as to provide an integral splint means 6.

In the embodiment 2, the plurality of elongated support members 12 is four, spaced equally around the base portion 10. It will be appreciated that the number of elongated support members 12 may be more or less than four.

Figures 1, 2:
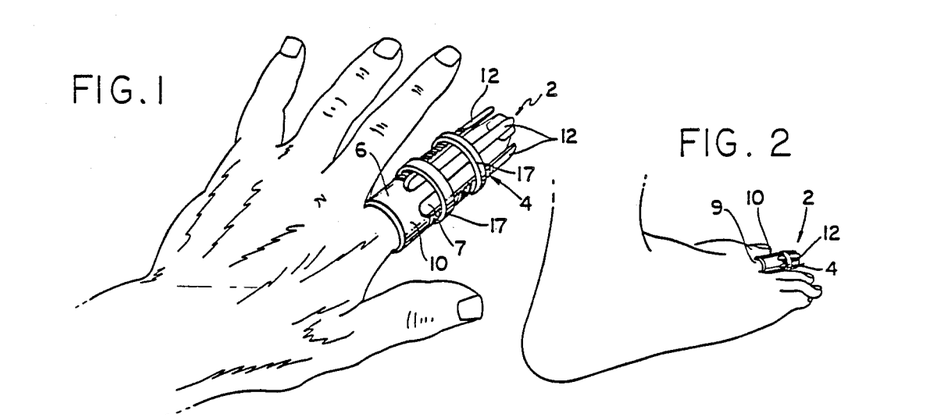
FIG. 1 is a perspective view showing an embodiment of the invention in place on a finger, and immobilizing same.
FIG. 2 is a perspective view showing an embodiment of the present invention in place on a toe.

As shown in FIGS. 1 and 2, the support members 12 terminate at the free end 13 which is in the vicinity of or extends past the distal end of a digit such as the finger 7 of FIG. 1 or the toe 9 of FIG. 2. Preferably, the free end 13 is very close to the distal end of the digit. This can be accomplished by cutting off any excess of the support member extending beyond the distal end of the digit to accommodate any length of digit.

In the embodiment 2, the plurality of support members 12 of the splint means 6 of the splint device 4 have a plurality of generally saw-toothed shaped projections 14 on the outer surfaces 15 thereof. The sawtooth projections 14 extend generally circumferentially.

Figures 3, 4, 5, 6:
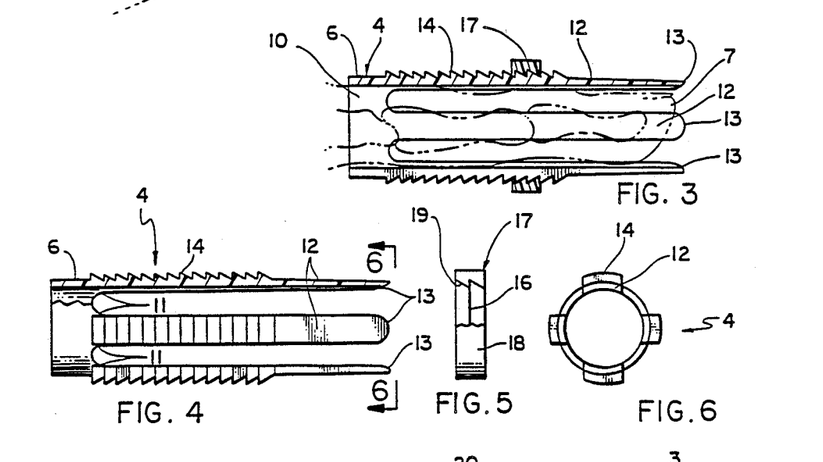
FIG. 3 is a longitudinal sectional view through a finger, showing how it is immobilized by the splint.
FIG. 4 is a side view, partially broken away, of the splint employed in FIG. 3.
FIG. 5 is a side view, partially broken away, of a compression means useful in the embodiment shown in FIG. 3.
FIG. 6 is a view taken along line 6—6 of FIG. 4.

The splint device 4 also comprises a compression means generally designated 17, as illustrated in FIG. 5. The compression means 17, in the embodiment 2, as illustrated in FIG. 5, is in the form of a ring having an outer surface 18 and and inner surface 19. The inner surface 19 is provided with a plurality of internal ridges, generally designated 16, which are complementary to the projections 14 on the support members 12 and the internal ridges 16 are adapted to engage the projections 14 to retain the compression means 17 thereon, as illustrated in FIGS. 1, 2, and 3. It will be appreciated that a plurality of compression means 17 may be provided having different internal diameters to provide varying degrees of compression to thereby accommodate various diameters of the body member to which it is applied.

In utilization, the splint means 6, when utilized, for example, on a fractured finger as illustrated in FIGS. 1 and 3, or a fractured toe as illustrated in FIG. 2, is slipped onto the digit from the distal end toward the proximal end thereof. Compression means 17, of an appropriate size, is selected and inserted around the support members 12 to the appropriate position desired. The diameter of the compression means 17 is selected to provide, at any given location along the axial extent of the support members 14, the desired degree of compression thereof. FIG. 1, for example, illustrates two such compression means 17 installed. The smaller the internal diameter of the compression means 17, the greater will be the degree of compression of the support members 12 against the digit to which it is applied. Therefore, by selecting the appropriate size of the compression means 17, the spacing apart of the support members 12 from each other may be varied throughout the axial length, from the base end 11 to the free end 13.

To remove the compression means 17 from the splint means 6, it is only necessary to compress the support members 12 toward each other so that the projections 14 are free of the internal ridges 16 and, when clear, the compression means 17 may be removed.

The splint device 4 may also comprise an end cap for engagement with the free ends 13 of the support members 12 to protect the distal end of the digit to which the splint device 4 is applied. Because of the preferred lightweight and semi-rigid characteristic of the material from which the splint means 6 is fabricated, it has been found that the free ends 13 may tend to catch on various objects and thus apply inadvertent and undesired strain or force to the digit.

Figure 7:
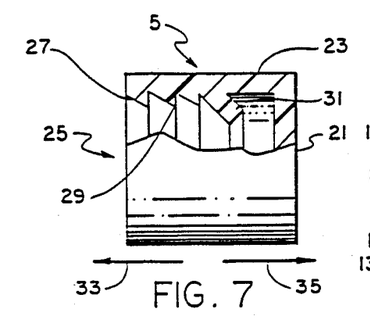
FIG. 7 illustrates an end cap means useful in the practice of the present invention.

An end cap, generally designated 5, is illustrated in FIG. 7, for utilization in the embodiment 2. The end cap 5, is fabricated in a generally cup-shaped configuration, having an end wall 21 and a circumferential wall 23. The end cap 5 has an open end 25 opposite the end wall 21. The internal surface 27, of the end cap 5 is provided with a plurality of ridges 29 which are generally the same as the ridges 16 of the compression means 17, and serve the same function. Utilization of the end cap 5, of course, requires that the projections 14, on the support members 12, extend to regions adjacent the free ends 13. The end cap 5 is pushed onto the plurality of support members 12, and the projections 14 thereon engage the ridges 29 to retain the end cap 5 in place.

If desired, the end cap 5 may be made "childproof" by any of the types of conventional childproof structures utilized in other applications. For example, an internal tab 31 may be provided on the internal surface 27, extending radially inwardly a greater distance than the ridges 29. When the internal tab 31 engages one of the projections 14, the flexibility of the material from which the preferred embodiment is made allows the internal tab 31 to bend toward the end wall 21 during installation. Therefore, it clears projections 14 when moved in the direction indicated by the arrow 33 to allow installation on the support member 12. The internal tabs, however, prevent inadvertent removal by engagement with the projections 14 when the end cap 5 is moved in the direction indicated by the arrow 35. Generally children will have difficulty depressing the support members 12 sufficiently to clear the internal tab 31, but adults will not be so hampered.

Thus, in the embodiment 2 of a splint device 4, as described above, there are three basic component parts: the splint means 6, the compression means 17, and, if desired, the end cap 5.

Figure 8:
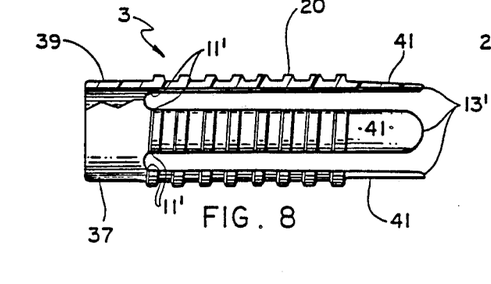
FIG. 8 is a side and partially broken away view of another embodiment of the invention.
Figure 9:
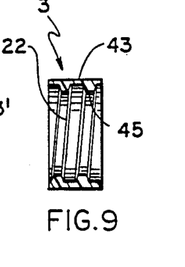
FIG. 9 is a sectional view of another compression means useful in the practice of the present invention.

FIGS. 8 and 9 illustrate another embodiment, generally designated 3, of the present invention, which is generally similar to the embodiment 2 described above.

In the embodiment 3 of a splint device generally designated 37, there is provided a splint means 39, generally similar to the splint means 6 described above, except that the projections 20 provided on the support members 41 are in the form of screw threads such as the Acme screw threads illustrated. A compression means 43, as illustrated in FIG. 9, is generally similar to the compression means 17 described above, except that the internal surface 45 thereof is provided with corresponding screw threads 22 for engagement with the screw threads 20 on the support members 41. The embodiment 3 may be utilized in a manner identical to that described above, except that the compression means 43 is threaded onto the splint means 39.

If desired, an end cap generally similar to the end cap 5 shown in FIG. 7, may also be utilized in the embodiment 3, except that the internal surface of such an end cap is provided with matching screw threads for engagement with the screw threads 20 on the support members 41.

It will be appreciated, of course, that a plurality of compression means 43 may be provided for installation on the splint means 39 and the internal diameters of the variety of compression means 43 may be varied so that differing degrees of compression may be obtained as the compression means 43 is threaded from the remote ends 13' of the support members 41 toward the base ends 11' thereof.

An end cap utilized in the embodiment 3 may, if desired, also be provided with childproofing, except that the internal tab, such as the internal tab 31 shown in FIG. 7, would extend circumferentially rather than axially, so that it would engage one of the support members 14 to prevent further unthreading thereof.

The materials from which the embodiments of the present invention may be fabricated may, for example, be polyvinyl chloride, polyvinyl propylene, nylon, or the like, as these materials, and other similar materials possess the desired degree of rigidity and flexibility, as well as lightness and minimal bulk preferred. Further, the various parts of the splint devices of the present invention are, preferably, injection molded to minimize the cost thereof.

Figure 10:
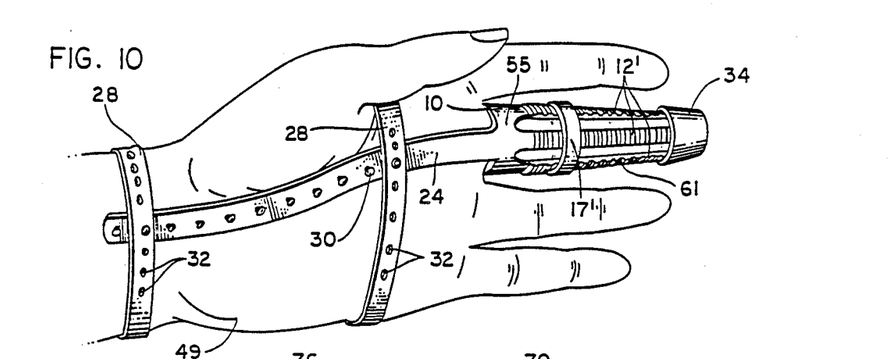
FIG. 10 is a perspective view of yet another embodiment of the present invention.

In some traumatic injuries to the digits, such as a fracture of the first bone of the digit, it may be necessary to immobilize the first knuckle joint, that is, the joint between, for a finger, the metacarpal of the hand, and the phalanx. In the case of the human foot, of course, the analagous joint to be immobilized is between the metatarsal and the phalanx or toe. FIG. 10 illustrates an embodiment generally designated 51 of the present invention to provide for such immobilization. As illustrated in FIG. 10, the splint device generally designated 53 of embodiment 51 is applied to a human hand, generally designated 49. As illustrated in FIG. 10, the embodiment 51 comprises a splint means 55, generally similar to the splint means 6 described above in connection with embodiment 2, or the splint means 39 described above in connection with the embodiment 3. The splint means 55 has a base portion 10' and a plurality of elongated support members 12'. A compression means 17' is shown installed as part of the splint device 53, and there is also provided an end cap 34, which is illustrated in greater detail in FIG. 13.

However, in the splint device 53, there is also provided a rearwardly extending rear support member 24 which extends from the base portion 10' in a direction opposite the direction of the elongated support members 12', and the rearwardly extending member 24 is positionable against the palm of the hand as illustrated in FIG. 10.

For application to the human foot, of course, the rearwardly extending member 24 would be positioned against the sole or bottom of the foot, extending toward the heel.

The rearwardly extending member 24 bears against the palm of the hand and, preferably, is comparatively rigid to prevent bending or curling of the fingers (or toes as the case may be). The rearwardly extending member 24 is, preferably, held in the position as illustrated in FIG. 10 by one or more restraining bands 28. Two such restraining bands are shown in FIG. 10. To provide for connection of the restraining bands 28 to the rearwardly extending member 24, a plurality of small protuberances 30 are incorporated on the rearwardly extending member 24. The restraining bands 28 have first walls generally designated 57, defining a plurality of apertures 32, which are so sized as to provide a substantially interference fit with the protuberances 30 on the rearwardly extending member 24. The restraining bands 28 may be fabricated from the same material as the splint means 55, compression ring 17' and end cap 34, or, alternatively, if resiliency as well as flexibility is desired, may be fabricated from a rubber-like material.

Figures 11, 12, 13, 14, 15, 16, 17, 18, 19, 21, 22, 23:
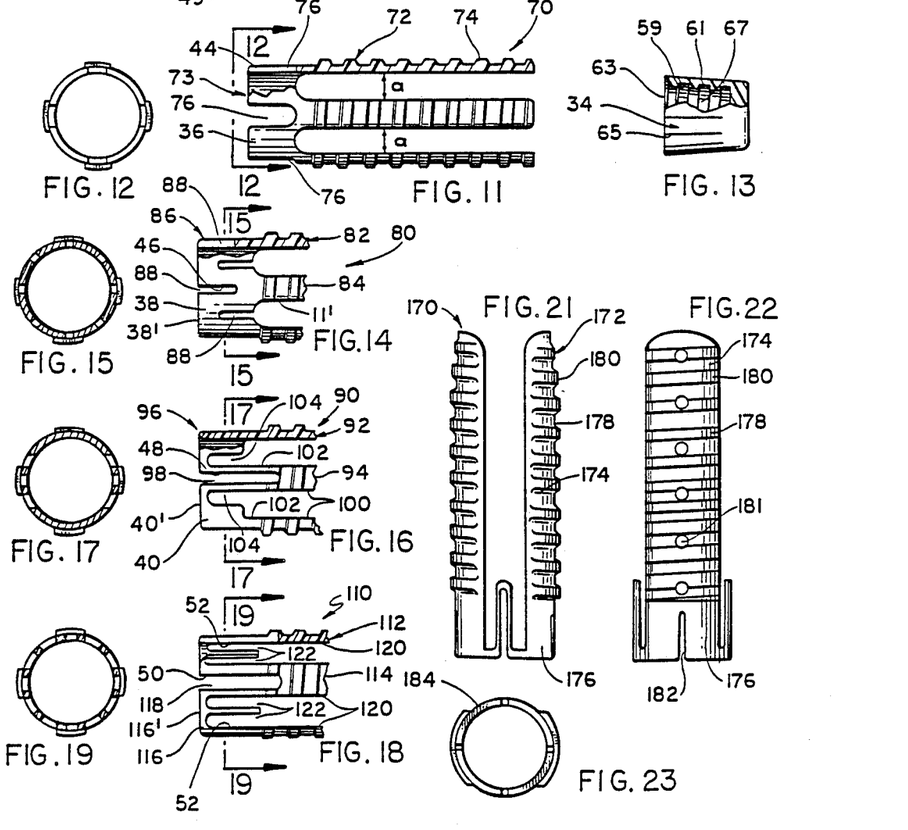
FIG. 11 is a side view, in partial section, of another embodiment of the present invention.
FIG. 12 is an end view of the splint of FIG. 11.
FIG. 13 is a side view, in partial section, of another end cap means useful in the practice of the present invention.
FIG. 14 is a partial view, in partial section, of another embodiment of the present invention.
FIG. 15 is a sectional view along the line 15—15 in FIG. 14.
FIG. 16 is a partial view in partial section of still another embodiment of the present invention.
FIG. 17 is a sectional view, taken along the line 17—17 in FIG. 16.
FIG. 18 is a partial view, in partial section, of another embodiment of the present invention.
FIG. 19 is a sectional view, taken along the line 19—19 in FIG. 18.
FIG. 21 is a side view of another embodiment of a splint of the present invention.
FIG. 22 is a side view 90° disposed from the view of FIG. 20, and shows breathing and drain holes.
FIG. 23 illustrates another compression means useful in the practice of the present invention.

The end cap 34, as illustrated in FIG. 13, is provided with internal screw threads 59 to match the screw threads 61 on the support members 12'. The end cap 34 may also be provided with a plurality of slits in the peripheral wall 61 thereof, adjacent the open end 63 to allow radial expansion thereof to accommodate different radial dimensions of the remote ends of the support members 12'. The end cap 34 may be utilized, for example, in the embodiment 3 as described above. Additionally, the end cap 34 may be made "childproof" in a manner similar to that described above, by providing an inwardly extending tab 67 on the inner surface 59, which during threading engagement with the threads 61 on the support members 12' freely rides over the threads, but in the unthreading thereof, engages the edges of one of the supporting members 12' to prevent further unthreading by a child. The cap may be radially distorted so that the tab 67 clears the members to allow complete removal of the end cap 34. Such radial deformation of the end cap 34 is generally beyond the capability of small children.

In the embodiments 2, 3, and 51, described above, the base portion of the splint means is of a tubular, ring-like configuration, having a given radial dimension. While, in the preferred embodiments, the semi-rigid characteristic of the material from which the splint means is fabricated allows radial deformation, the circumferential extent of the base portion is fixed. It has been found that, in accordance with the principles of the present invention, in many applications it is desirable to have a circumferential expansion capability in the base portion, while still retaining the basic tubular configuration on a body member as described herein. Additionally, the base portion of the present invention may be selectively fabricated in any desired cross-sectional shape, such as round, as illustrated herein, or other shapes to accommodate specific body members.

The circumferential expansion capability allows utilization of the splint device of the present invention on a variety of different sized body members. Such circumferential expansion capability, together with the radial deformation capability, increases the utility of the splint devices according to the principles of the present invention.

The circumferential expansion capability may be provided by incorporating expansion joints in the base portion of the splint means.

FIGS. 11 and 12 illustrate an embodiment of the present invention generally designated 70, in which there is provided a splint means 72, which, in general, is similar to the splint means 6 and 37 described above in that it comprises a base portion 36 and a plurality of support members 74 extending therefrom. However, in the embodiment 70, the base portion 36 of the splint means 72 has an expansion means 73, generally comprised of first walls 44 defining a slot 76 aligned with each of the support members 74 and the slot 76 extends into the support members 74. As illustrated in FIGS. 11 and 12, the slots 76, together with the spacing "a" between adjacent support members 74, allow a radial expansion of the base portion 36 which thereby allows a circumferential expansion of the base portion 36 to accommodate different sized digits.

FIGS. 14 and 15 illustrate another embodiment of the present invention, generally designated 80, in which there is illustrated a splint means, generally designated 82, having a base portion 38 and a plurality of elongated support members 84 extending therefrom. Expansion means, generally designated 86, are provided in the base portion 38 of the splint means 82 by means of walls 46 defining a plurality of slots 88. As illustrated in FIGS. 14 and 15, the slots 88 are in staggered, overlapping, configuration, with alternating slots 88 extending from regions adjacent the base end 11' of the elongated support members 84 into the base portion 38, and other slots 88 extending from the remote end 38' of the base portion 38. The slots 88 thereby allow radial expansion and circumferential expansion of the base portion 38 to accommodate a variety of digit sizes.

It will be appreciated, of course, that slots or cut-outs of various sizes and arrangements may be provided in the splint means of the present invention to provide the expansion means for the circumferential expansion capability of the base portion. Such expansion means, such as the expansion means 86 described above in connection with FIGS. 14 and 15 and the expansion means 73, described above in connection with the embodiment 70 of FIGS. 11 and 12, are but two structures providing such circumferential expansion capability.

FIGS. 16 and 17 illustrate another embodiment, generally designated 90, of a splint device 92 according to the principles of the present invention, having a splint means 94. The splint means 94 (as well as the splint means 72 and 84 of the embodiments 70 and 80, respectively, described above) may be generally similar to the splint means 6 and 37 described above. However, the expansion means, generally designated 96, in the base portion 40 of the splint means 94, is provided with first walls 48 defining slots 98, extending axially from the remote end 40' of the base portion 40, through the base portion and into each of the support members 100. Second walls, generally designated 102, are also provided in the expansion means 96, to define slots 104 extending into the base portion 40 in a direction opposite the slots 98. The expansion means 96 of FIGS. 16 and 17 allows even greater circumferential expansion than the expansion means 86 and 73 described above.

FIGS. 18 and 19 illustrate yet another embodiment, generally designated 110, of a splint device 112 having a splint means 114. The splint means 114 is generally similar to the splint means 6 and 37 described above, and is provided with a base portion 116, having a remote end 116'. The base portion 116 has first walls, generally designated 50, defining slots 118, extending through the base portion 116 and into the support members 120, similar to the slots 98 described above in connection with the embodiment 90 illustrated in FIGS. 16 and 17. However, in embodiment 110 there are provided second walls 52 defining a pair of slots 122 between adjacent support members 120, to provide even greater allowable circumferential expansion.

Figure 20:
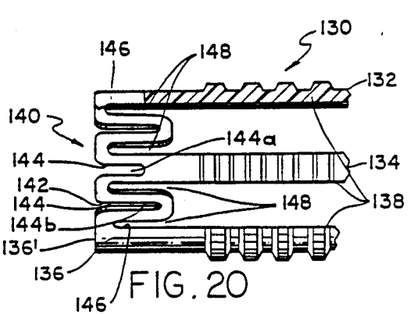
FIG. 20 is a partial view, partially in section, of another embodiment of the present invention.

FIG. 20 illustrates yet another embodiment, generally designated 130, of the present invention, providing expansion capability in the base portion. As illustrated in FIG. 20, there is provided a splint device 132, having a splint means 134, which is provided with a base portion 136, having a remote end 136' and a plurality of elongated support members 138 extending from the base portion 136. The expansion means 140 of the embodiment 130, is achieved by first walls 142 in the base portion 136, defining a plurality of slots 144 extending into the base portion from the remote end 136' thereof, both in alignment with each of the support members 138, as illustrated at 144a, as well as intermediate each of the support members 138 as illustrated at 144b. The base portion 136 also has second walls 146, defining a pair of slots 148, between each of the support members 138. The expansion means 140 provides an even greater allowable circumferential expansion of the base portion 136.

It will be appreciated, of course, that many variations of slots may be provided, as well as other structures to achieve the desired circumferential expansion capability.

It will also be appreciated, of course, that while the embodiments 70, 80, 90, 110, and 130, described above are illustrated as incorporating threads on the supporting members, projections such as the projections 14 in embodiment 2 described above, could also be utilized, as could any of the other projections as described herein, on each of these embodiments. Further, appropriate restraining means and end caps may also be incorporated as desired with any of these embodiments.

In the embodiments above described, the base portion was permanently coupled, for example, by molding, to the supporting members. However, in some applications, it may be desired to provide the base portion as a separate structure from the supporting members.

Figures 24, 25:
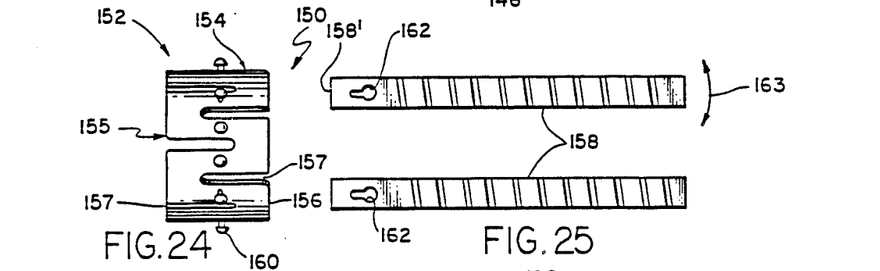
FIGS. 24 and 25 illustrate another embodiment of the present invention.

FIGS. 24 and 25 illustrate an embodiment, generally designated 150, of a splint device, generally designated 152, having a splint means, generally designated 154, comprised of a base portion 156 and a plurality of separate support members 158. The base portion 156 is a ring-like structure and may be circumferentially non-extendible, similar to the base portion 10, for example, described in connection with embodiment 2 above. Alternatively, it may be provided with any of the expansion means described above. As illustrated in FIG. 24, the base portion 156 is provided with expansion means generally designated 155, which, for example, may comprise a plurality of slots 157, and is generally similar to the expansion means 86, as illustrated in FIGS. 14 and 15. However, any other desired type of expansion means may equally well be utilized in the base portion 156.

The base portion 156 is also provided with a plurality of spaced apart radially extending "mushroom" shaped projections 160, in a predetermined spaced array around the circumference. The projections 160 are illustrated in a circumferentially aligned array. However, the projections may, if desired, be in a circumferentially staggered relationship.

A plurality of support members 158 may be utilized with the base portion 156. As illustrated in FIG. 25, the support member 158 is provided with at the base end 158' thereof with a "keyhole" shaped slot therethrough, generally designated 162. The keyhole shaped slot is adapted to be positioned over the mushroom shaped projections 160 for removable coupling on the base portion 156. It will be appreciated that embodiment 150 allows for the positioning of the support members 158 in other than the fixed locations as provided in the embodiments described and illustrated above. Thus, the attending personnel utilizing the splint device 152 may position several support members 158 closely adjacent each other on the base portion 156, and leave other areas free of support members. Depending upon the type of injury to the body member upon which the splint device 154 is applied, the positioning of the support members 158 around the base portion 156 will provide not only immobilization and/or protection, but may also provide access to other portions of the body member for which more frequent treatment may be required. Thus, the utilitarian value of the present invention is further enhanced by the structure of embodiment 150 in particular applications where access to various portions of the injured body member is required, and yet the splint type function is also necessary. In embodiment 150, the support members 158 are shown with projections comprising screw threads similar to that illustrated in embodiment 3 described above. It will be appreciated that the saw-tooth type projections as illustrated in embodiment 2, or any of the other projections on the support members as described herein, may advantageously be utilized.

Embodiment 150 also provides another advantage in that the support members 158 may be pivotally rotated in the directions indicated by the arrow 162 after installation on the base portion 156. This additional feature allows the attending personnel to provide even greater positional capability of the support members along the injured body member to which the splint device 154 is applied. In other applications, however, it may be desired to provide a more secure coupling between the support members 158 and the base portion 156. Such more secure or permanent type coupling may be provided by appropriately bonding, by a suitable adhesive or the like.

Thus, in accordance with the principles of the present invention, the support members of a splint device may be unitarily fabricated and thus fixedly coupled to the base portion, they may be detachably coupled, or any combination thereof.

FIGS. 21, 22, and 23, illustrate another embodiment, generally designated 170, of the present invention, in which there is provided a splint device, generally designated 172, having a splint means 174, comprised of a base portion 176, and a plurality of support members 178, coupled to the base portion 176. As illustrated in embodiment 170, there are two such support members 178 coupled to the base portion 176, and in diametrically opposed relationship. Projections such as the screw threads 180 may be provided on the support members 178, although, it will be appreciated, any of the other projections on the support members, as described herein, may be advantageously utilized in embodiment 170. Further, the base portion 176 is shown as including expansion means 182, which, in general, is similar to the expansion means 140 described in connection with FIG. 20. However, as illustrated in embodiment 170, the two support members 174 are of greater circumferential extent and thus more rigid than the support members described above. In certain applications, the more rigid type of support member may be desired to provide additional protection and/or immobilization to a given body member to which the splint device 172 is applied. As shown more clearly in FIG. 22, the support members 178 may be provided with a plurality of apertures 181 extending therethrough. Such apertures 181 allow for the drainage of water or perspiration from the body member to which it is applied.

It has been found that embodiment 170 is advantageously utilized on a body member over which bandages or other types of dressings or the like have previously been applied for treatment of the injured body member.

The splint device 172 may also comprise a compression means such as the compression means 184 illustrated in FIG. 23, which is provided with internal threads matching the threads 182 on the support members 178. An appropriate end cap, such as the end cap 34 shown in FIG. 13, may also be utilized as required. Because of the greater circumferential extent and more massive structure associated with embodiment 170, it has been found that such an embodiment may be advantageously utilized on body members comprising not only the digits, but also any appropriate other body member such as arms, legs, or the like, to the extent that such structure may be appropriately installed and utilized.

Figure 26:
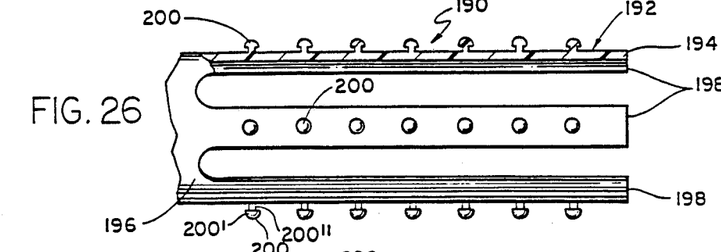
FIGS. 26, 27, and 28 illustrate another embodiment of the present invention.

FIGS. 26, 27, 28, and 29 illustrate another embodiment, generally designated 190, of a splint device, generally designated 192, of the present invention. The splint device 192 comprises a splint means generally designated 194, having a base portion 196 and a plurality of support members 198, coupled thereto. Base portion 196, as illustrated in FIG. 26, is shown as unitarily molded with the support members 198. However, it will be appreciated that the support members 198 may be detachably coupled to the base portion 196 in a manner as illustrated in embodiment 150, described above. Further, the base portion 196 is shown as a circumferentially fixed base portion. The base portion 196 may, if desired, be provided with expansion means to provide circumferential expansion capability as described above.

Integral with the support members 198, there are provided a plurality of "mushroom" shaped projections generally designated 200, extending therefrom. In the preferred structure of embodiment 190, the mushroom shaped projections 200, on each of the support members 198 are in an axially spaced apart array and are axially spaced a preselected distance from the mushroom shaped projections on each of the other support members 198, to provide an axially staggered non-circumferentially aligned array. The mushroom shaped projections 200 have a head portion 200' and a stem portion 200''.

Figure 27:
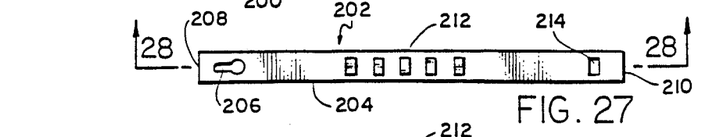
Figure 28:
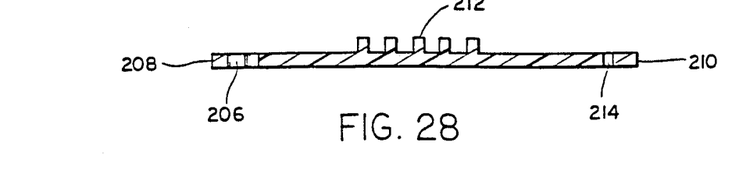

FIGS. 27 and 28 illustrate a compression means, generally designated 202, usefull with the splint means 194 illustrated in FIG. 26. As illustrated in FIG. 27, the compression means 202 is a strap-like member 204, having a "keyhole" shaped aperture, generally designated 206 therethrough, in regions adjacent a first end 208 which is disposed in a spaced apart relationship to a second end 210 thereof. Intermediate the first end 208 and second end 210 of the strap-like means 204, there is provided a plurality of upstanding catch means 212. Adjacent the second end 210, there is provided a catch receiving aperture 214 which is adapted to engage one of the upstanding catch means 212. In utilizing the compression means 202 with the splint means 188 of the splint device 194, the keyhole shaped aperture 206 is placed over the mushroom shaped projection 200 and the enlarged portion of the keyhole shaped aperture allows it to fit over the head 200' of the mushroom shaped projection 200. The stem 200'' of the mushroom shaped projection 200 is then positioned in the slot of the keyhole shaped aperture 206, and the restraining means 202 is wrapped around the splint means 194. The aperture 214 is then positioned over one of the catch means 212 for securing of the strap means 204. The axially staggered relationship of the mushroom shaped projections 200 on each of the support members 198 allows the strap-like member 204 to be securely wrapped on the splint means 194. It will be appreciated that, depending upon the particular configuration of the body member to which the splint device 192 is applied, the various support members 198 may be in radially different positions so that restraining means 202 may engage less than all of the support members 198. As many restraining means 202 may be utilized on the splint means 194 in as many locations as desired.

Figures 29, 30, 31, 32, 33:
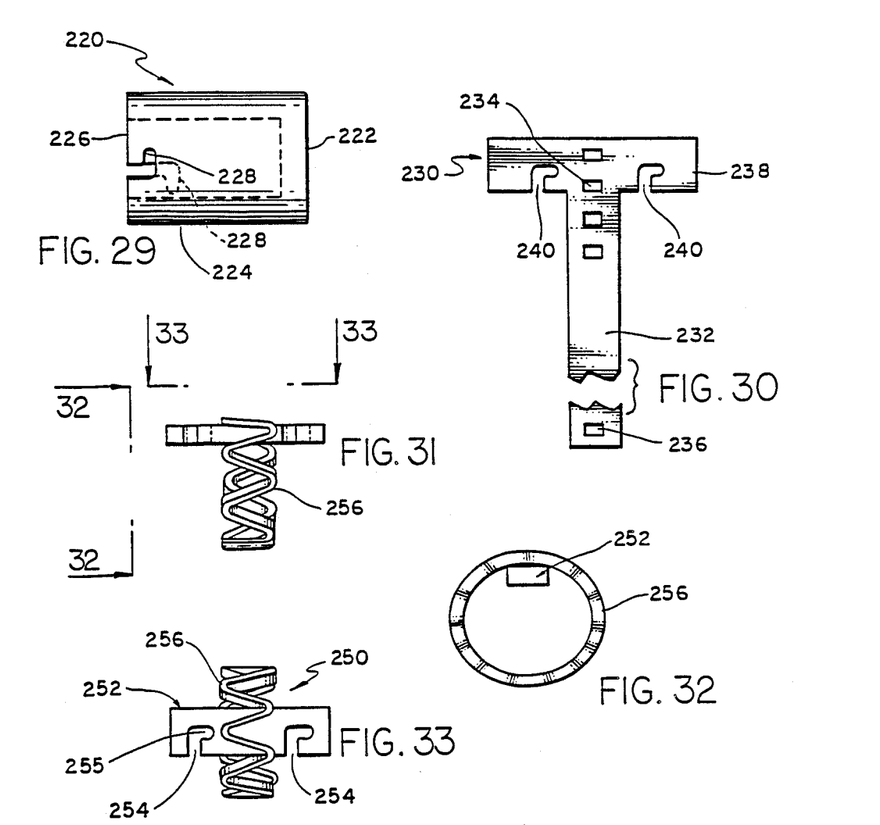
FIG. 29 illustrates another end cap means useful in the practice of the present invention.
FIG. 30 illustates another compression means useful in the practice of the present invention.
FIGS. 31, 32, and 33 illustrate another compression mean useful in the practice of the present invention.

A cap means, generally designated 220, is illustrated in FIG. 29, and has particular utility with embodiment 190. The cap means 220 is generally similar to the cap means described above, having an end wall 222 and a peripheral wall 224. However, the open end 226 is provided with a pair of opposed slots 228, diametrically opposed from each other in the peripheral wall 224 which engage and lock onto the mushroom shaped projections 200 of the support members 198.

FIG. 30 illustrates another compression means, generally designated 230, which is useful in the practice of the present invention and, in particular, embodiment 190 described above. The compression means 230 is generally similar to the compression means 202 in that it is provided with a strap-like portion 232, upon which there are provided a plurality of catch means 234 and a catch receiving aperture 236. There is also provided a head portion 238, extending substantially at right angles to the strap portion 232 and the head portion 238 has a pair of mushroom engaging apertures 240 therein. The mushroom engaging apertures 240 are spaced apart a distance corresponding to the axial spacing of the mushroom shaped apertures 200 on the support members 198. In applying the compression means 230, mushroom accepting apertures 240 are positioned adjacent a pair of mushroom shaped projections 200 on any of the support members 198 and moved in the direction of arrow 241 to "lock" the compression means 230 in place. The strap portion 132 wrapped around the digit and/or additional support members 198, and the aperture 236 is positioned on one of the catch means 234 for retention thereon. It will be appreciated that more than one of the compression means 230 or compression means 202 may be utilized in conjunction with the splint means 194.

Figure 34:
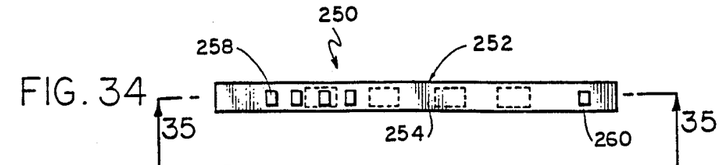
FIG. 34 is a side view of element 252 in FIGS. 32 and 33.
Figure 35:
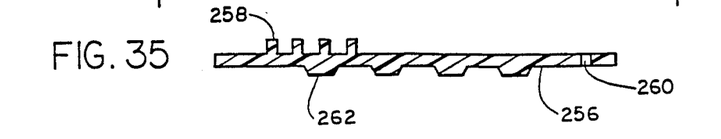
FIG. 35 is a section taken along line 35—35 in FIG. 34.

The compression means illustrated above in connection with embodiments 2, 3, and 10, have generally been ring-shaped members. It has been found, however, that strap-like compression means may also be advantageously utilized with such embodiments which incorporate either thread-like projections on the external surface of the support members, or saw-toothed type projections on the support members, or, alternatively, on those embodiments wherein there are not provided any projections on the support members. FIGS. 33 and 34 illustrate a compression means, generally designated 250, which may be advantageously utilized with splint means of the type described herein, either having projections on the external surfaces of the support members or free of such projections on the support members. As illustrated in FIGS. 33 and 34, the compression means 250 comprises a strap-like member 252, having an outer surface 254, and an inner surface 256. The strap-like member 252 is adapted to be wound around the splint means upon which it is utilized. The strap-like member 252 is also provided with catch means 258, extending outwardly from the outer surface 254 and a catch receiving aperture 260 is provided for engagement with one of the catch means 268. A plurality of support member engaging projections 262 extend outwardly from the inner surface 256 of the strap means 252. The support member engaging projections 262 engage the sides of the support members of a splint means of the present invention. The catch receiving aperture 260 is positioned over one of the catch means 258. It will be appreciated that one or more of the compression means 250 may be advantageously utilized in any splint device described herein. Further, the compression means 250 need not be positioned externally all of the support members on any one splint means, but may be intertwined as desired to provide a particular compression configuration.

The ring-like compression means, such as the compression means 12 and 22 described above, have a fixed circumferential extent. In some applications, it may be desirable to provide a compression means which has circumferential expansion capability. FIGS. 31, 32, and 33 illustrate a restraining means, generally designated 250, having such a circumferential expansion structure. The compression means 250, illustrated in FIGS. 31, 32, and 33, is particularly adapted for utilization with the splint means 194 illustrated in FIG. 26. However, it will be appreciated that suitable modifications to such a structure may make it adaptable to any of the splint devices described herein, by inclusion, for example, of internal projections such as the internal projections 262 described above in connection with FIGS. 33 and 34.

As illustrated in FIGS. 31, 32, and 33, the compression means 250 has a head portion 252, generally similar to the head portion 238, and is provided with walls 253 defining a pair of slots 254, adapted to engage adjacent mushroom shaped projections 200 on a support member 198. The slots 254 are in spaced apart relationship, corresponding to the axial spacing between adjacent mushroom shaped projections 200.

The compression means 250 also comprises an expansion ring 256 which is generally similar to a spring-like ring which is resiliently flexible. As shown, the expansion ring 256 is in a generally Z-shaped configuration, and the cross-sectional areas associated with each part of the expansion ring 256, together with the material from which it is comprised, defines both the expansion capability and resiliency thereof. As noted above, when the compression means 250 is desired to be utilized with other embodiments of the present invention, including those which have saw-tooth type projections, or those embodiments in which there are no projections on the external surface, internal projections on the head portion 252 may be provided, corresponding to the circumferential spacing between adjacent support members on a splint device according to the principles of the present invention. In such applications, where the mushroom shaped projections 200 are not provided, then the slots 254 need not be provided.

It will be appreciated that, in addition to the preferred types of compression means described herein, in certain applications, it may be desired to utilized conventional rubber bands, adhesive type tape, or the like, to provide the desired compression to the splint means and the body member to which the splint means is applied.

In embodiments of the present invention which have been fabricated, it has been found that, for applications to digits such as a finger or toe, the nominal diameter of the base portion may be on the order of 1" and in the range of ¼" to 1½". Expansion means may, of course, in those embodiments incorporating such structure, increase the circumference of the base portion to values greater than that provided by the nominal diameter. In those embodiments incorporating four elongated support members molded integrally with the base portion, it has been found that such support members may be substantially equally spaced around the circumference of the base portion and on the order of ¼" wide in the circumferential direction. The thickness of the base portion and support members may be on the order of 1/16" to ⅛", although greater or lesser thicknesses may be utilized as desired. The axial length of the elongated support members may be on the order of 3", but may be severed to any desired length.

The circumferential extent of the support members 174 of embodiment 170 of FIGS. 21, 2, and 23 may, in order to provide more rigid support, be on the order of ¾" in circumferential extent.

The compression means may be fabricated to provide compression diameters when installed on the order of ¼" to 1½", although longer or smaller dimensions may be utilized in particular applications.

Figure 36:
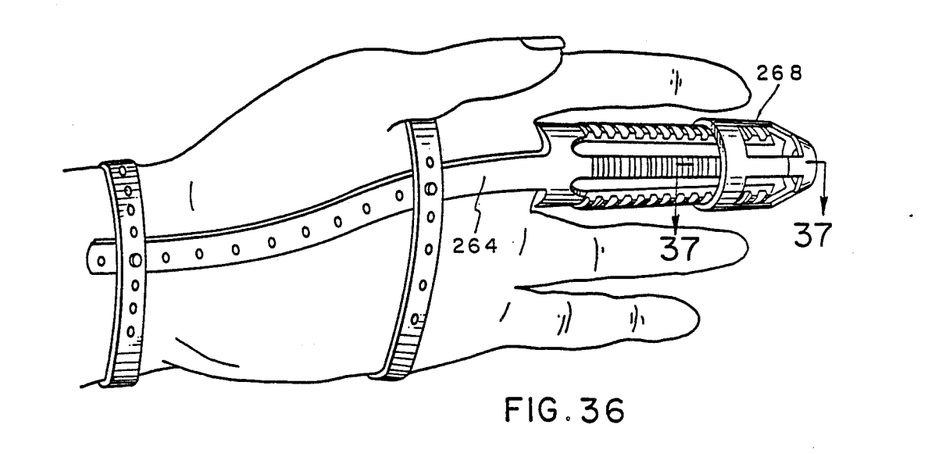
FIG. 36 is a perspective view of another and preferred embodiment of this invention.
Figure 37:
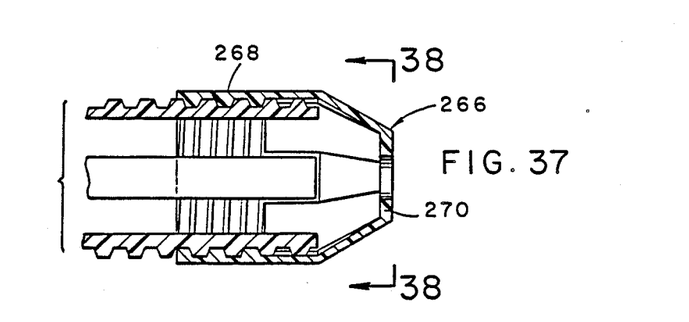
FIG. 37 is a sectional view along line 37—37 in FIG. 36.
Figure 38:
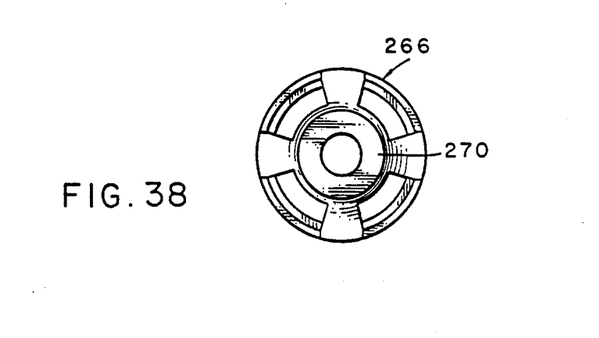
FIG. 38 is an end view from line 38—38 in FIG. 37.

In FIGS. 36 to 38, the splint 264 has an end cap 266. The end cap 266 has a ring portion 268 and end portion 270 in a unified structure which cojoins the function of the separate rings and end caps discussed above.

Figures 39, 40, 41:
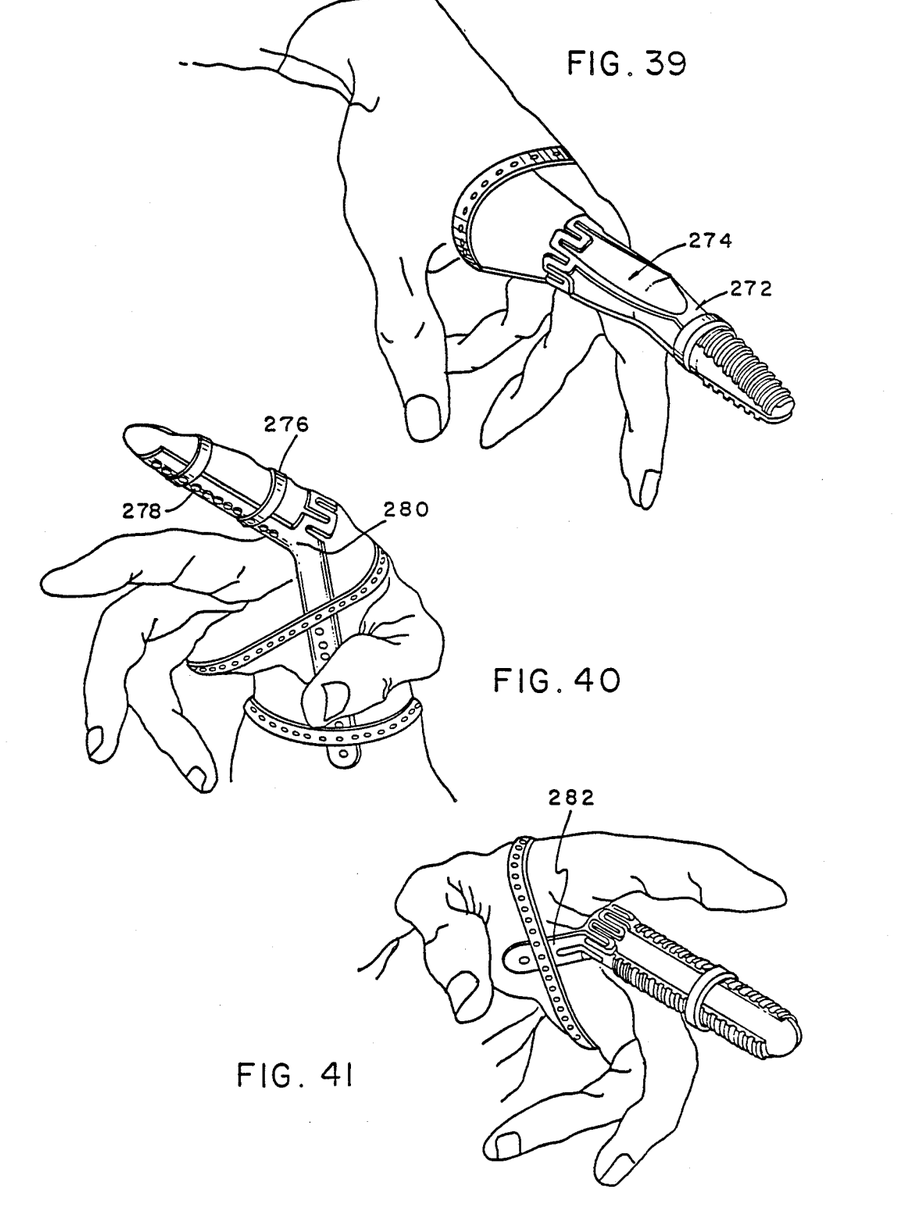
FIG. 39 is a perspective view of another embodiment of this invention.
FIG. 40 is a perspective view of a different embodiment of the invention.
FIG. 41 is also a perspective view of still another different embodiment of the invention.

FIGS. 39 to 41 show preferred splints. Splint 272 has an opening 274 to permit some flexing of the finger at the knuckle. The embodiment of FIG. 40 has two rubber rings 276 each of which have holes receiving projections 278 extending from the bottom surface of the splint 280. In FIG. 41 the element 282 is less extensive than element 24 of FIG. 10, allowing for wrist flexure.

Figures 42, 44:
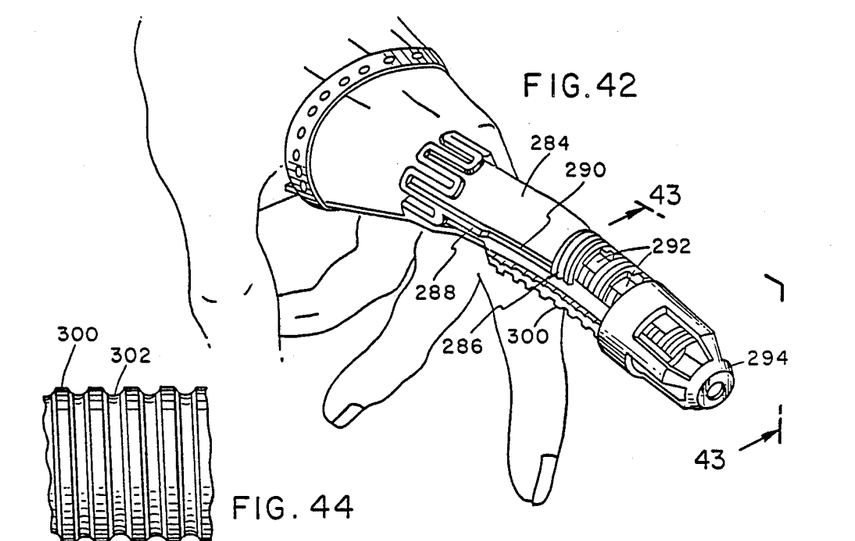
FIG. 42 is a perspective view of the most preferred embodiment of the invention.
FIG. 44 is a side view taken along line 44—44 in FIG. 43.
Figures 43, 45, 46:
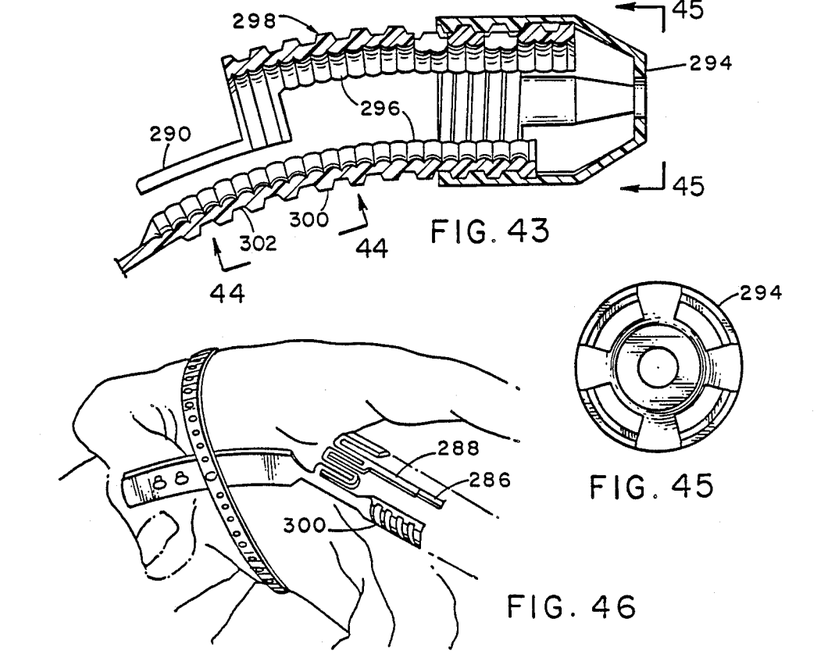
FIG. 43 is a section taken along line 43—43 in FIG. 42.
FIG. 45 is an end view from line 45—45 in FIG. 43.
FIG. 46 is an underside perspective view of the device of FIGS. 42-45.

FIGS. 42 to 44 show opening 284. The elements 286 at each side of the figure have a thicker portion 288 and a thinner portion 290. The thinner portion 290 can flex when the knuckle is flexed. The thicker portion 288 is essentially rigid, thus a kind of hinge-like action is provided. The openings 292 provide air flow for sweat evaporation and drainage of the contained body member for better cleanliness and comfort for the patient. The end cap 294 is as has been already discussed. The end cap generally extends from the distal end of the finger rearwardly past the first joint so that the ring portion of the end cap provides compression force rearwardly of the first joint for maximum effect and comfort. The end cap can be partially unscrewed to reduce compression, if desired, such as when swelling occurs.

The inner surface 296 of the splint which normally abuts the contained body member have grooves and ridges as shown to facilitate drying and air circulation. The exterior surface 298 of the underside of the splint is provided with a series of lands 300 and grooves 302. The splint is normally made of plastic and the grooves 302 being of lesser thickness are adapted to take a "crease" or "set" when the splint is manually bent so that the splint can be set on any desired degree of curvature and thereby better conform to the configuration of the body member.

From the above, it can be seen that there has been provided an improved splint device which is comparatively inexpensive, rapidly and easily applied and removed, and adaptable to a variety of body members.

Those skilled in the art may find many variations and adaptations of the invention, and all such adaptations and variations falling within the true scope and spirit of the invention, are intended to be protected by the appended claims.

I claim:

1. An improved splint device for the immobilization of a body member, comprising, in combination:
    a splint means having:
        a tubular base portion, and the body member insertable in the tubular base portion;
        at least one elongated support member having a base end coupled to said tubular base portion and a free end spaced from said base end, said at least one support member positionable adjacent the body member for immobilizing support thereof;
        said at least one support member further comprises a plurality of projections thereon extending outwardly therefrom in a preselected spaced array between said base end and said free end thereof; and removable end cap means positionable on said free end of said at least one support member, the cap having a recess opening toward the base portion for receiving and protecting the end of the body part adjacent thereto.

2. The splint device defined in claim 1 and further comprising:
at least one compression means removably positionable around said at least one support member and the body member and intermediate said base end and said free end of said at least one support member in said adjacent position to the body member.

3. The splint device defined in claim 1 wherein:
said at least one support member is fixedly joined to said base portion.

4. The splint device defined in claim 1 wherein:
said at least one support member and said base portion are removably joined together.

5. The splint device defined in claim 1 wherein:
said at least one support member is pivotally joined to said base portion.

6. The splint device defined in claim 1 wherein:
said base portion further comprises expansion thereof.

7. The splint device defined in claim 1 wherein:
said at least one support member further comprises walls defining at least one aperture therethrough and said at least one aperture between said base end and said free end.

8. The splint device defined in claim 2 wherein:
said compression means further comprises means for releasably engaging said projections on said at least one support member for securing said restraining means at a preselected location thereon.

9. The splint device defined in claim 1 wherein:
said cap means further comprises means for releasably engaging said projections on said at least one support member for securing said cap means thereon in regions adjacent said free end thereof.

10. The splint device defined in claim 1 wherein:
said compression means further comprises means for releasably engaging such projections in said at least one support member for securing said compression means at a preselected location thereon.

11. The splint device defined in claim 1 wherein:
said projections on said at least one support member comprise saw tooth shaped projections.

12. The splint device defined in claim 11 wherein:
said compression means is ring-shaped, having an internal surface and further comprises saw tooth shaped ridges on said internal surface thereof for releasable securing engagement with said at least one support member.

13. The splint device defined in claim 1 wherein:
said projections on said at least one support member comprise saw tooth shaped projections;
said compression means in ring-shaped, having an internal surface and further comprises saw tooth shaped ridges on said internal surface thereof for releasable securing engagement with said saw tooth projections on said at least one support member;
said cap means is cup-shaped, having an end wall and peripheral wall, and said peripheral wall having an inner surface, and further comprises saw tooth shaped ridges on said inner surface of said peripheral wall for releasable securing engagement with said saw tooth projections on said at least one support member in regions adjacent said free end thereof.

14. The splint device defined in claim 13 wherein:
said at least one support member further comprises walls defining at least one aperture therethrough and said at least one aperture between said base end and said free end.

15. The splint device defined in claim 1 and further comprising:
a rearwardly extending rear support member coupled to the base portion and extending therefrom in a direction opposite to the direction of said elongated support member and positionable adjacent another body member for providing increased support to the body member in said splint device.

16. The splint device defined in claim 15 and further comprising:
strap means positionable around said rear support member and said other body member for maintaining said rear support member adjacent said other body member.

17. The splint device defined in claim 16 wherein:
said strap means has walls defining a plurality of apertures therethrough for engagement with said projections on said rear support member.

18. The splint device defined in claim 1 wherein:
said projections on the said at least one support member comprise screw thread type projections.

19. The splint device defined in claim 18 wherein:
said compression means is ring-shaped, having an internal surface and further comprises screw thread type projections on said internal surface for threading releasable engagement with said screw thread type projections on said at least one support member.

20. The splint device defined in claim 1 wherein:
said cap means is cup-shaped, having an end wall and peripheral wall, and said peripheral wall having an inner surface, and said cap means further comprises screw thread projections on said inner surface of said peripheral wall for threading engagement with said screw thread type projections on said at least one support member in regions adjacent said free end thereof.

21. The splint device defined in claim 2 wherein:
said at least one compression means further comprises walls defining mushroom shaped projection receiving apertures therein for engaging said mushroom shaped projections on said at least one support member; and
said end cap means further comprises walls defining mushroom shaped projection receiving apertures for engagement with mushroom shaped projections in regions adjacent said free end of said at least one support member.

22. The splint device defined in claim 21 wherein:
said base portion further comprises a support end adjacent the coupling of said elongated support members thereto and a remote end spaced a preselected distance from said support end;
said expansion means further comprises walls in said base portion comprising a plurality of spaced apart slots extending from said remote end a preselected distance into said ring portion toward said support end thereof.

23. The splint device defined in claim 22 wherein:
said base portion further comprises walls defining a second plurality of spaced apart slots extending from said support end a preselected distance toward said remote end.

24. The splint device defined in claim 23 wherein:
said first plurality of slots and said second plurality of slots are in overlapping, spaced apart, relationship.

25. The splint device defined in claim 2 wherein:
said compression means further comprises a strap-like means, and catch means thereon for releasably restraining said compression means in said position around said at least one support member and the body member.

26. The splint device of claim 1 wherein the end cap is integrally formed with a compression means removably positioned around at least one support member.

27. The splint device of claim 1 wherein the support member has on at least part of its internal surface grooves and ridges to facilitate drying.

28. The splint device of claim 1 wherein the support member has at least on opening therethrough to facilitate airflow.

29. The splint device of claim 1 wherein the exterior surface of the splint member has a series of lands and grooves whereby the support member is adapted to be manually set at any desired degree of curvature.

30. An improved splint device for the immobilization of a body member, comprising, in combination:
a splint means having:
a tubular base portion, and the body member insertable in the tubular base portion, said tubular base portion having a remote end and a support end spaced from the remote end;
a plurality of elongated support members having a base end coupled to said support end of said tubular base portion and a free end spaced from said base end, and said plurality of support members positionable adjacent the body member for immobilizing support thereof;
a plurality of projections on each of said support members extending radially outwardly therefrom; and
removable end cap means positionable on said free ends of said support members, the cap having a recess opening toward the base portion for receiving and protecting the end part of the body part adjacent thereto.

31. The splint device defined in claim 30 wherein:
the number of said plurality of support members is two, and said two support members are coupled to said support end of said base portion in a circumferentially spaced apart relationship.

32. The splint device defined in claim 30 wherein:
each of said support members has a circumferential dimension on the order of ¾ of an inch.

33. The splint device defined in claim 30 and further comprising:
compression means removably positionable around said support members, intermediate said base end and said free ends thereof, for retaining said support members in said adjacent position to the body member.

34. The splint device defined in claim 33 wherein:
said compression means are ring-shaped.

35. The splint device defined in claim 34 wherein:
said projections on said support members comprise threads;
said compression means comprises internal threads for threading engagement with said support members.

36. The splint device defined in claim 30 wherein:
said end cap is generally cup-shaped, and further comprises internal threads for threading engagement with said threads on said support members in regions adjacent the free ends thereof.

37. The splint device defined in claim 30 wherein:
the number of said plurality of support members is four, and said four support members are coupled to said support end of said base portion in a circumferentially spaced apart relationship.

38. The splint device defined in claim 37 wherein:
each of said support members has an circumferential dimension on the order of ¼ of an inch.

39. The splint device defined in claim 33 wherein:
said compression means are ring-shaped.

40. The splint device defined in claim 39 wherein:
said projections on said support members comprise threads;
said compression means comprises internal threads for threading engagement with said support members.

41. The splint device defined in claim 40 and further comprising:
end cap means positionable on said free ends of said support members for protecting the end of the body part adjacent thereto.

42. The splint device defined in claim 41 wherein:
said end cap is generally cup-shaped, and further comprises internal threads for threading engagement with said threads on said support members in regions adjacent the free ends thereof.

43. The splint device defined in claim 31 and further comprising:
the expansion means in said base portion of said splint means.

44. The splint device defined in claim 43 wherein:
the thickness of said base portion and the thickness of said support members are on the order of 1/16 to ⅛ of an inch;
the nominal diameter of said base portion is in the range of ¼ inch to 1½ inches; and
the length of said support members is on the order of 3 inches;
and said compression means comprises a plurality of ring-like compression means providing compression diameters on the order of ¼ inch to 1½ inches.

* * * * *

UNITED STATES PATENT AND TRADEMARK OFFICE
CERTIFICATE OF CORRECTION

PATENT NO. : 4,813,406

DATED : March 21, 1989

INVENTOR(S) : GEORGE B. OGLE, II

It is certified that error appears in the above-identified patent and that said Letters Patent is hereby corrected as shown below:

Col. 17, line 12 (Claim 2, line 7), after "member" insert -- for retaining said at least one support member --

Col. 17, line 24 (Claim 6, line 3), before "thereof" insert -- means for circumferential expansion --

Col. 17, line 52 (Claim 12, line 5), after "said" insert -- saw tooth projections on said --

Col. 19, line 44 (Claim 30, line 20), delete "part"

Signed and Sealed this

Twelfth Day of February, 1991

Attest:

HARRY F. MANBECK, JR.

*Attesting Officer*      *Commissioner of Patents and Trademarks*